(12) United States Patent
Matthews

(10) Patent No.: US 6,197,055 B1
(45) Date of Patent: Mar. 6, 2001

(54) SINGLE CHAMBER MECHANICAL HEART

(76) Inventor: Herbert L. Matthews, 21-4360 Emily Carr Drive, Victoria B.C (CA), V8X 4Y4

( * ) Notice: Subject to any disclaimer, the term of this patent is extended or adjusted under 35 U.S.C. 154(b) by 0 days.

(21) Appl. No.: 09/347,298

(22) Filed: Jul. 6, 1999

(51) Int. Cl.[7] .................................................. A61M 1/10
(52) U.S. Cl. ........................ 623/3.11; 623/3.1; 417/472
(58) Field of Search .................... 623/3.11, 3.18, 623/3.22, 3.23, 3.24, 3.25; 600/16; 417/50, 97, 98, 472

(56) References Cited

U.S. PATENT DOCUMENTS

| | | |
|---|---|---|
| 3,734,648 | 5/1973 | Nielson . |
| 4,058,857 * | 11/1977 | Runge et al. .................... 623/3.11 |
| 4,221,548 * | 9/1980 | Child .................... 623/3.11 |
| 4,547,911 | 10/1985 | Strimling . |
| 4,650,485 * | 3/1987 | Della Sala .................... 623/3.11 |
| 4,869,656 * | 9/1989 | Della Sala .................... 623/3.11 |
| 5,549,667 | 8/1996 | Davidson . |
| 5,578,077 | 11/1996 | Kassatly . |

FOREIGN PATENT DOCUMENTS

| | | |
|---|---|---|
| 1234953 | 4/1988 | (CA) . |
| 2105908 | 3/1995 | (CA) . |
| 2105935 | 3/1995 | (CA) . |

* cited by examiner

Primary Examiner—Bruce Snow
(74) Attorney, Agent, or Firm—Baker McLachlen

(57) ABSTRACT

A single chamber mechanical heart has a movable vane journaled in the apex of the casing, an inlet port and an outlet port in each side wall of the chamber, and means for mechanically reciprocating the vane to pump blood on either side of the vane. The vane can be electromagnetically positioned using electro magnets or a shaft drive through the chest of the patient. The blood pressure and rate can be controlled by appropriate motion of the vane.

3 Claims, 3 Drawing Sheets

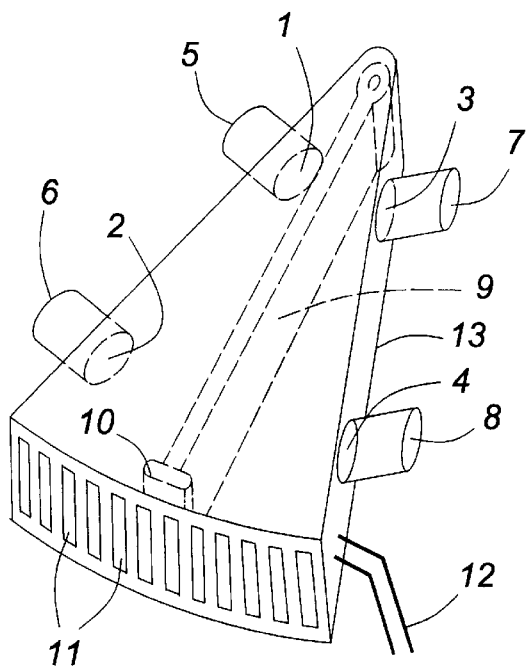
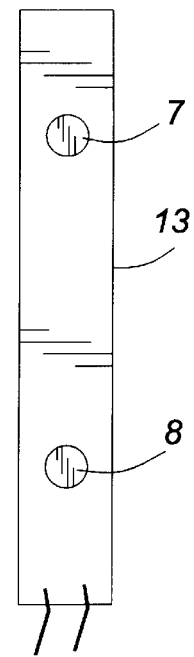
FIG. 1
FIG. 2
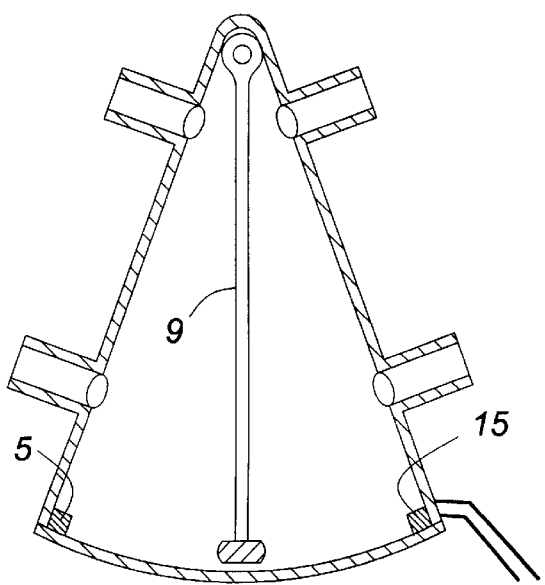
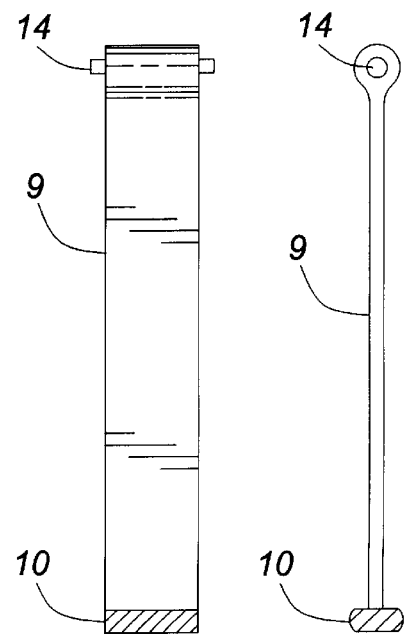
FIG. 3
FIG. 4  FIG. 5

SINGLE CHAMBER MECHANICAL HEART

FIELD OF THE INVENTION

The present invention relates to a total artificial mechanical heart for use in replacement of a human heart. In particular, the invention relates to such a device which has a single pumping chamber.

BACKGROUND OF THE INVENTION

Numerous efforts have been made to replace a defective human heart with a mechanical device which replicates the pumping action of a normal human heart. Canadian published patent applications 2,105,908 and 2,105,935 to Mussivand et al, filed Sep. 10, 1993 both relate to hydraulically actuated mechanical pumps for duplicating blood pumping action of the human heart. A right ventricular assist device is shown in Canadian patent 1,234,953 which utilizes an elliptical chamber with a flexible diaphragm separating a sac for connection to the patient's blood system and a pressurizing chamber for augmenting the flow of blood from the sac.

U.S. Pat. No. 3,734,648 relates to a mechanical heart which injects a driving fluid into one side of a diaphragm dividing a chamber to cause the evacuation of blood from the opposite side of the chamber. The system includes a piston pump and an accumulator for the driving fluid. U.S. Pat. No. 5,578,077 of Nov. 26, 1996 teaches the use of a scroll type pump modified for medical applications. U.S. Pat. No. 5,549,667 teaches an external mechanical heart having blood contacting parts made of Zirconium and alloys thereof. U.S. Pat. No. 4,547,911 of Oct. 22, 1995 relates to an implantable heart pump which runs at a harmonic multiple of a normal heart beat frequency, thereby reducing the pump chamber volume.

Thus many inventors have attempted to duplicate the pumping action of the human heart in an implantable mechanical heart.

SUMMARY OF THE INVENTION

The present invention provides a single chamber mechanical heart which duplicates the function of a human heart with minimum moving mechanical parts, thus providing a simple reliable mechanism suitable for implantation in the chest of a patient in the space formerly occupied by a human heart. In one embodiment, the heart pumping action is powered by an electromagnetically operated diaphragm vane, with electrical connections to an external power source, which controls the pulse rate as well as the volume of blood pumped. In a second embodiment the pump is powered by a mechanical shaft extending through the skin of the patient. This shaft is rotated in an oscillatory fashion causing motion of the diaphragm vane to pump the blood. In this second embodiment, the pulse rate as well as the blood pressure are controlled by external drive mechanisms controlled by sensors connected to the patient.

BRIEF DESCRIPTION OF THE DRAWINGS

In the accompanying drawings,

FIG. 1 is a phantom perspective of a first embodiment of the invention,

FIG. 2 is a side view of the embodiment of FIG. 1,

FIG. 3 is a view of embodiment of FIG. 1 with the top removed to show the diaphragm vane, FIGS. 4 and 5 are side and top views of the vane.

DETAILED DESCRIPTION OF THE PREFERRED EMBODIMENTS

Figure 6:
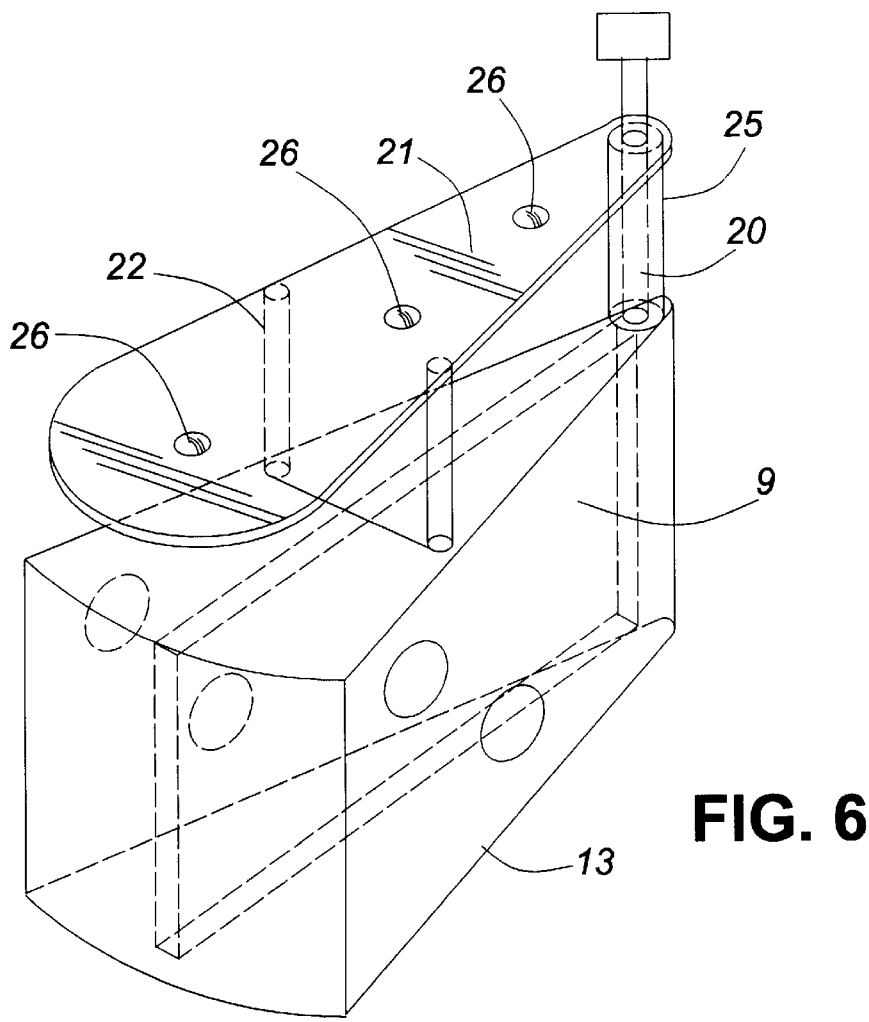
FIG. 6 is a phantom perspective of a second embodiment of the invention.

With reference to FIG. 1 there is shown a first embodiment of the invention, including a case 13, a vane 9 and valves 1,2,3,4. A plurality of electromagnets 11 are energized by a power supply (not shown),via a cable 12 and attract the magnetic end 10 of vane 9 to successive positions along the arc of the casing 13 under control of the power supply. The sequence of energizing the magnets 11 is normally from one end of the array to the other, the rate being determined by the pulse rate to be provided to the patient. The volume of each stroke of the mechanical heart is determined by the distance the vane travels along the arc. Ports 5,6,7 & 8 are connected to the arteries and veins normally, with blood from the one side of the pump being circulated to the pulmonary system, and blood from the other side of the pump being circulated to the aorta, and to the vena cava whence it is returned to the first side of the pump.

By using a single vane to pump both sides of the artificial heart, a simple efficient mechanism is obtained which can effectively replace the human heart.

Specifically, port 5 is connected to the Superior Vena Cava, and Inferior Vena Cava, drawing blood from both when the vane 9 is moving away from the port 5. Port 6 is supplying blood to the Pulmonary Artery, which supplies blood to the lungs. Port 7 is receiving blood from the Pulmonary Vein, and port 8 is connected to the Aorta, taking oxygenated blood to all parts of the body.

FIGS. 4 and 5 are respectively a side view and top view of the vane 9. One end of the vane has bearing means 14 fitted for rotation in depressions in the top and bottom surfaces of the case 13. Magnet member 10 on the free end of the vane 9 is moved in response to the energization of the array of magnets 11, by the external power supply. The speed of motion of the vane 9 is regulated by well known current control means in the power supply.

The chambers of each side of the vane can be made of a size to accommodate the actual cardiac output of the patient. Once the cardiac output has been determined the artificial heart may then be made to order. Stops 15 in each corner of the case 13 prevent the vane from crushing blood cells against the sides of the case.

For a mechanical heart to be implantable in a human chest, it must meet specific requirements; it must not weigh more than about 300 grams, or ¾ pound, it must fit into a chest cavity of approximately 5.5×3×3.5 inches, it must be stable within the chest, it must not crush blood cells, it must not cause blood clotting, it must pump the correct volume of blood at the correct pressure, and it must have a reliable power source. By having a residual amount of blood in the chamber at all times, blood clotting should be prevented, as there will always be a mixing and blood will be mixed and moved on either to the lungs or as oxygenated blood to serve the body.

Figure 7:
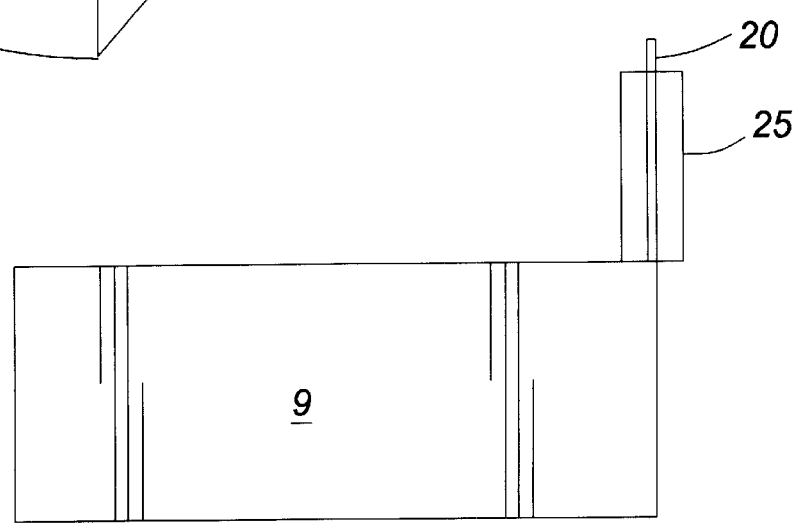
FIG. 7 is a side view of the vane of FIG. 6.
Figure 8:
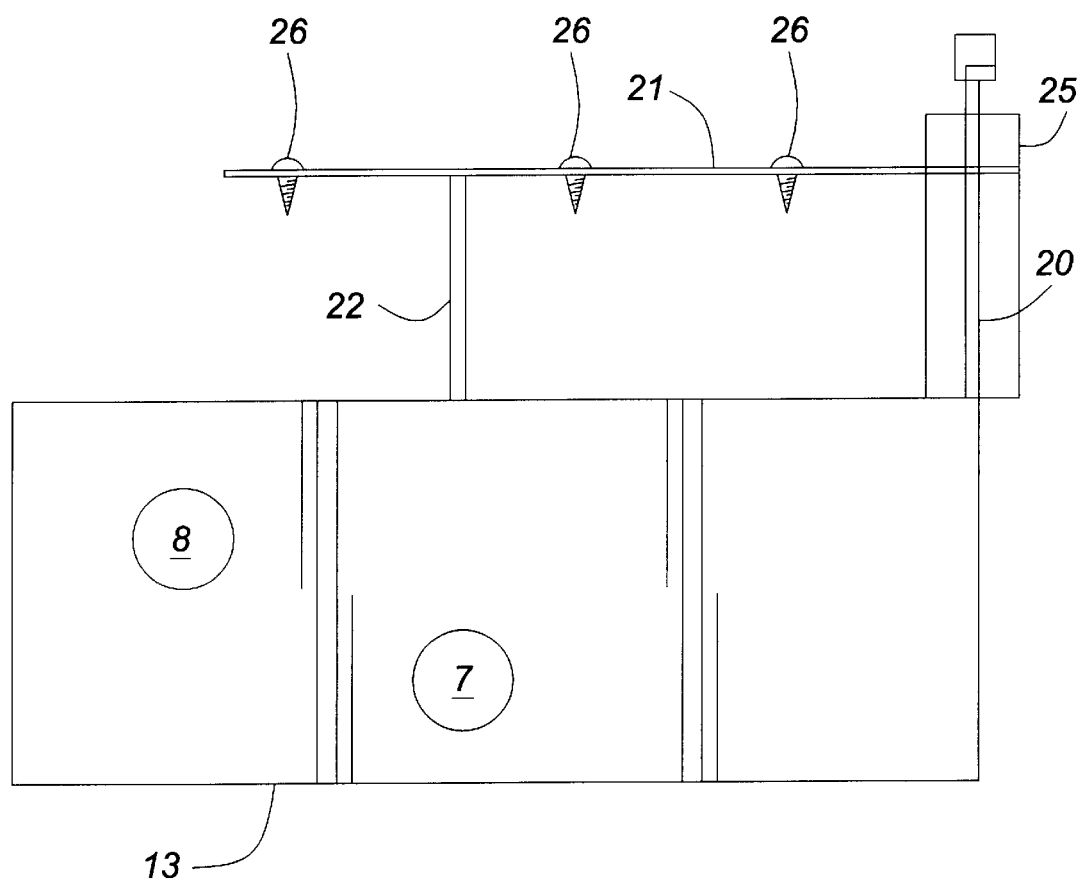
FIG. 8 is a side view of the second embodiment.

A mechanically driven embodiment of the mechanical heart is shown in FIGS. 6,7,& 8. As before, a casing 13 encloses a vane 9 which is attached to a shaft 20 which will extend through the skin of the patient in a housing 25, and be connected to a reciprocating mechanical drive (not shown). A plate 21 is fastened to the exterior of the case 13, with pillars 22, and is connected to the sternum of the patient by screws 26 to stabilize the position of the heart in the chest cavity of the patient. As before blood is pumped by reciprocation of the vane 9 in the cavity 13. Preferably the corners of the chamber 13 will be rounded, as will the edges of the ports 5,6,7 & 8, and some blood should be left in the chamber at the end of each stroke so there will always be a mixing action and blood will be moved on, and not remain in the chamber to clot.

Stabilizing the unit to the sternum will not be difficult, since the distance between the pumping unit and the under side of the sternum is small. The top side of the sternum center section is only slightly convex, and the plate 20 could extend over the sides of the sternum onto the cartilage that joins the ribs to the sternum. The screws26 in the sternum make a rigid connection to the unit 13. The hole in the chest in the skin will allow the shaft 20 to protrude about ½ inch, above the skin. The hole is of course stabilized in one position by the plate 21 being anchored to the sternum. The skin will heal round the housing 25 to maintain cleanliness.

The casing 13 and the plate 21 are solidly joined so that the casing 13 will move in the the chest with movement of the rib cage and the sternum. Coughing will move it around, so there must be a flexible section in the shaft connected to shaft 20. A simple variable speed electric motor and control can easily be positioned on the body of the patient.

The exact position of the stabilizing pillars 22 will depend on the the lie of the person's heart. Each heart is tailor made to fit the position of the damaged heart it replaces. The cavity created by the removal of the damaged heart must be filled by the mechanical heart and its outer molded shell around the casing 13. As the mechanical heart must pump about ⅓ of a cup of blood at a time using a single chamber, it will not be very big and will weigh about 300 grams. The volume or cardiac output, the weight and size of the damaged heart can be ascertained and the mechanical heart designed to fit perfectly. In installing the mechanical heart, a heart/lung machine would be attached to the large blood vessels in the leg of the patient. The custom made mechanical heart whether electromagnetically or mechanically driven, would be put in place and set to operate with a heart lung machine still in place, until the mechanical heart takes over the circulation of blood.

What is claimed is:

1. A single chamber mechanical heart, having a casing in the shape of a circular sector of a cylinder, with upper and lower faces, an apex, and a curved circumferential wall opposite said apex and straight side walls joined at said apex a movable vane having a first end journaled in said apex, said vane extending substantially between said upper and lower faces, and a second end adjacent said curved circumferential wall an inlet port and an outlet port in each side wall of said chamber, and magnetoeletric drive means comprising said second end of said vane having a magnetically susceptible portion, and a plurality of circumferential surface and adapted to be energized by an electric current passing through one or more of said magnets for causing reciprocating rotation of said vane about said journal, said vane dividing said chamber into two segments of variable size as said vane moves toward and away from each side wall of said chamber, whereby blood is pumped into and out of each of said segments through said inlet and outlet ports by reciprocal motion of said vane.

2. A single chamber mechanical heart, having a casing in the shape of a circular sector of a cylinder, with upper and lower faces, an apex, and a curved circumferential wall opposite said apex and straight side walls joined at said apex, a movable vane having a first and journaled in said apex, said vane extending substantially between said upper and lower faces, and a second end adjacent said curved circumferential wall, an inlet port and an outlet port in each side wall of said chamber, and means for causing reciprocating rotation of said vane about said journal, said vane dividing said chamber into two segments of variable size as said vane moves toward and away from each side wall of said chamber, whereby blood is pumped into and out of each of said segments through said inlet and outlet ports by reciprocal motion of said vane and further comprising a shaft connected to said first end of said vane for reciprocal rotary motion, said shaft being contained within a housing for extending through the skin of a patient and adapted to be driven by an external motor to cause reciprocation of said vane.

3. A mechanical heart as claimed in claim 2, and having means for attaching said casing to the sternum of a patient.

* * * * *

UNITED STATES PATENT AND TRADEMARK OFFICE
CERTIFICATE OF CORRECTION

PATENT NO.     : 6,197,055 B1
DATED          : March 6, 2001
INVENTOR(S)    : Herbert L. Matthews It is certified that error appears in the above-identified patent and that said Letters Patent is hereby corrected as shown below:

<u>Column 4,</u>
Line 12, after "plurality of" insert -- electrically energizable magnets located in said --
Line 25, delete "and" and insert -- end --

Signed and Sealed this

Thirtieth Day of October, 2001

*Attest:*

*Attesting Officer*

NICHOLAS P. GODICI
*Acting Director of the United States Patent and Trademark Office*